US007145043B2

(12) United States Patent
Zhu

(10) Patent No.: US 7,145,043 B2
(45) **Date of Patent: *Dec. 5, 2006**

(54) NON-HAZARDOUS OXIDATIVE NEUTRALIZATION OF ALDEHYDES

(75) Inventor: Peter Zhu, Irvine, CA (US)

(73) Assignee: Ethicon, Inc., Somerville, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/013,681

(22) Filed: Dec. 16, 2004

(65) Prior Publication Data

US 2005/0107631 A1 May 19, 2005

Related U.S. Application Data

(63) Continuation of application No. 10/349,363, filed on Jan. 22, 2003, now Pat. No. 7,012,163.

(51) Int. Cl.
*C07C 45/00* (2006.01)

(52) U.S. Cl. ...................... 568/492; 568/426; 568/433; 568/438; 568/445; 568/458; 568/493

(58) Field of Classification Search ..................... None
See application file for complete search history.

(56) References Cited

U.S. PATENT DOCUMENTS 6,399,850 B1 6/2002 Chen et al.
6,776,904 B1 8/2004 Zhu et al.

FOREIGN PATENT DOCUMENTS

JP 7204661 8/1995

OTHER PUBLICATIONS

H. Y. Cheung, M. R. Brown, "Evaluation of glycine as an inactivator of glutaraldehyde," 34 J. Pharm. 211 (1982).

Japanese Abstract (English Equivalent of Patent No.: JP 407204661A (Application No. JP06004416), "Treatment Agent of Waste Glutaraldehyde Liquid and Treatment of Waste", Aug. 8, 1995.

English Translation of Japanese Patent Application No. H6-4416 ; Filing Date Jan. 20, 1994.

Seyhan N. Ege, "Organic Chemistry, Structure and Reactivity", Third Edition, 1994m o, 534-535.

Non-confidential correspondence and literature from KEM Medical Products Corp.- Dated Feb. 28, 2001 ; Product Brochures (Glut-RX™ Glutaraldehyde Solution Neutralizer, KemSure™ OPA Solution Neutralizer, Neutralizing Spill Control Kits for glutaraldehyde, Neutralizing Absorbent Mats for Glutararaldehyde, Neutralizing Absorbent Mats of OPA, Neutralizing Spill Control Kits of OPA, Safety Nozzles) ; Results of Toxicity Test conducted From Nov. 29 Through Dec. 3, 2000 With a Neutralized Cidex™ OPA Solution, Jan. 2001 ; Results of Toxicity Test Using Neutralized Cidex™ Solution Conducted from Oct. 18 Through 22, 2000 Dec. 2000.

Merck Index, Eleventh Edition, pp. 4732 & 8532 (1989).

*Primary Examiner*—Sikarl A. Witherspoon
(74) *Attorney, Agent, or Firm*—Theodore Shatynski

(57) ABSTRACT

Methods, compositions, and devices for alleviating the problems of toxic discharge of aldehydes present in waste streams are disclosed. The methods relate to forming neutralized aldehydes by treating aldehydes with oxidizing agents. The oxidizing agents offer a simple, effective, fast and inexpensive solution for treatment of toxic aldehydes prior to disposal into the environment.

9 Claims, 1 Drawing Sheet

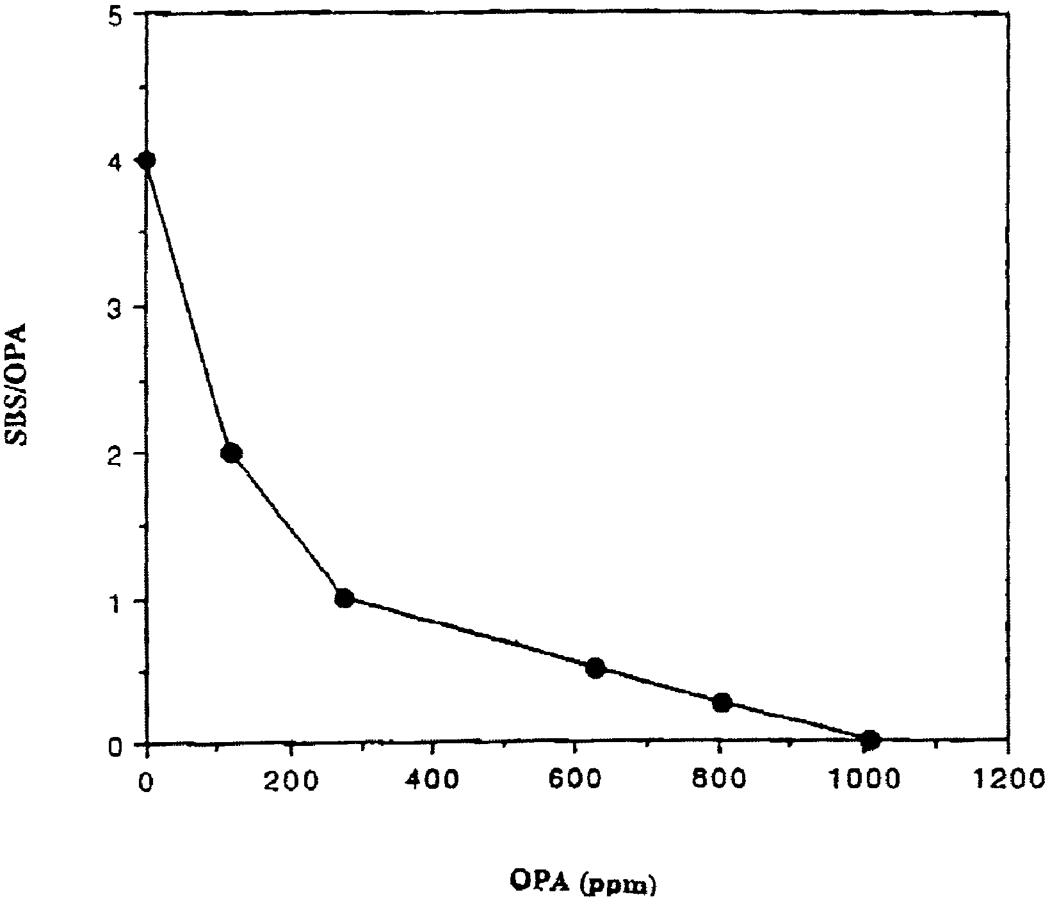
SBS/OPA
5
4
3
2
1
0
0
200
400
600
800
1000
1200
OPA (ppm)

NON-HAZARDOUS OXIDATIVE NEUTRALIZATION OF ALDEHYDES

RELATED APPLICATIONS

This application is a continuation of U.S. Ser. No. 10/349,363, filed Jan. 22, 2003 now U.S. Pat. No. 7,012,163 entitled NON-HAZARDOUS OXDATIVE NEUTRALIZATION OF ALDEHYDES, which application is related to patent application U.S. Ser. No. 09/896,589, filed Jun. 29, 2001 entitled "NON-HAZARDOUS BASIC NEUTRALIZATION OF ALDEHYDES", the disclosure of which is incorporated by reference.

The complete disclosures of the aforementioned related U.S. patent applications are hereby incorporated herein by reference for all purposes.

BACKGROUND OF THE INVENTION

1. Field of the Invention

The invention relates to neutralization of aldehydes for the purpose of complying with waste disposal requirements established by federal and state environmental protection agencies, in particular, with forming non-reversible neutralized aldehydes which are non-hazardous and do not revert back to toxic aldehydes.

2. Description of Related Art

Waste disposal of aldehydes has become increasingly more difficult over the years. Treatment of wastes containing a certain amount of aldehyde prior to placement of the waste into the environment is required by law. The extent of such treatment may vary depending upon the location of where the waste is generated and the stringency of the environmental standards in that area. For example, waste containing aldehyde may be classified as a hazardous waste in California under 22 CAL. CODE REGS., TIT. 22, § 66696. Formaldehyde also may be considered a hazardous waste on the federal level under 40 C.F.R. § 261.33(e) if it is a commercial chemical product (e.g., pure technical grade formaldehyde or formaldehyde is the sole active ingredient of the product that is to be disposed). Every state has an environmental regulation that is at least as stringent as this formaldehyde standard. State regulations also may be more stringent than this standard.

Additionally, facilities that discharge waste water to Publicly Owned Treatment Works ("POTW") or directly into navigable waters may be required to meet standards that are established by a government agency. The standard may vary for each facility depending upon the quality of the receiving water and the concentration of aldehyde found in the waste water that is discharged into the environment by industry in that area.

Waste containing aldehyde may be generated by a variety of processes. For example, aldehydes such as glutaraldehyde and o-phthalaldehyde ("OPA") are used in disinfecting medical devices or instruments. Waste containing aldehydes also may be generated by painting operations, stripping operations related to floors, or other manufacturing operations.

Typically, ammonia and sodium bisulfite ("SBS") are used to treat many aldehydes. These compounds, however, have not proven to be effective at neutralizing OPA in accordance with environmental regulations.

A waste is classified as a hazardous waste in California if the waste being examined "has an acute aquatic 96-hour $LC_{50}$ less than 500 milligrams per liter (mg/L) when measured in soft water (total hardness 40 to 48 milligrams per liter of calcium carbonate) with fathead minnows . . . . " 22 CAL. CODE REGS., TIT. 22, § 66696. $LC_{50}$ represents the concentration of a waste that is necessary to kill 50% of a particular animal exposed to a waste.

Note that a nonhazardous waste is generally considered by federal and state environmental agencies as a waste that does not satisfy the criteria set forth in defining a hazardous waste. Therefore, wastes generated in California that have a $LC_{50}$>500 mg/L are nonhazardous wastes and wastes having $LC_{50}$<500 mg/L are classified as hazardous. SBS, for example, in combination with OPA, produces a product that is generally considered hazardous under California environmental law as shown in Table 1 by $LC_{50}$ being consistently below 500 mg/L. For this study, CIDEX® OPA (commercially available from Advanced Sterilization Products®, a Johnson & Johnson Company of Irvine, Calif.) was used to supply the OPA.

TABLE 1

Neutralization Of OPA Using SBS

| Sample Type | OPA Content (%) | $LC_{50}$ (mg/L) | Comments |
|---|---|---|---|
| Fresh CIDEX ® OPA at 0.3% OPA | 0.301% | 31.1 mg/L | 1 |
| Fresh CIDEX ® OPA at 0.15% OPA | 0.158% | 50.4 mg/L | 2 |
| Reuse CIDEX ® OPA at 0.3% OPA | 0.295% | 31.1 mg/L | 3 |
| SBS/OPA = 4:1 | N/A | 68.3 mg/L | 4 |
| SBS/OPA = 2:1 | N/A | 46.3 mg/L | 5 |

1. Fresh CIDEX ® OPA at 0.3% OPA was prepared by diluting the fresh Cidex OPA solution with deionized water.
2. Fresh CIDEX ® OPA at 0.15% OPA was prepared by diluting the fresh Cidex OPA solution with deionizedwater to the level of 0.15% of OPA.
3. Reuse of CIDEX ® OPA at 0.3% OPA was prepared by diluting the simulated reuse CIDEX ® OPA (14 days) with deionized water.
4. SBS/OPA = 4:1, 10% SBS (10 mL) was combined with 100 mL of the fresh CIDEX ® OPA solution at 0.3% OPA (sample 1 above) at the SBS/OPA molar ratio of 4 to 1 for 30 minutes, and then the combined solution was used in the 22 CAL. CODE REGS., TIT. 22, § 66696 test for California.
5. SBS/OPA = 2:1, 10% SBS (5 mL) was combined with or 100 mL of the fresh CIDEX ® OPA solution at 0.3% OPA (sample 1 above) at the SBS/OPA molar ratio of 2 to 1 for 30 minutes, and then the combined solution was used for the fish test in the 22 CAL. CODE REGS., TIT. 22, § 66696 test for California.

In addition to lacking the ability to effectively neutralize OPA, ammonia and SBS are problematic since they may be harmful to the environment.

FIG. 1 shows that when OPA is combined with SBS at the molar ratio of SBS/OPA=4:0 for 30 minutes, OPA has been neutralized since the OPA concentration is nondetectable in a high performance liquid chromatography (HPLC) analysis method, which has detection limit for OPA at 10 ppm. However, the end product is still classified as a hazardous waste as shown in Table 1. Therefore, even though the aldehyde is neutralized completely by a neutralizer, the end product may still be a hazardous waste.

The purpose of this invention is to invent an effective, non-hazardous, convenient and inexpensive neutralizer for glutaraldehyde, o-phthalaldehyde (OPA) and/or other aldehydes. Glutaraldehyde and o-phthalaldehyde are the main chemicals used in industry and hospital for high-level disinfection. The glutaraldehyde or o-phthalaldehyde needs to be neutralized after use before disposal, however, at this point, there are only very limited neutralization methods available. Commonly assigned patent application U.S. Ser. No. 09/321,964, entitled "ALDEHYDE NEUTRALIZER" suggests using amino acids such as glycine as neutralizers.

While use of glycine offers an inexpensive, fast and non-hazardous solution to aldehyde neutralization, there are, however, some problems with the amino acid neutralizer approach. One problem is that Schiff's base solutions formed between o-phthalaldehyde and glycine is black. In Japan, the general feeling is that they do not like black color; therefore, hospitals send their used solution to the waste treatment companies for disposal, which is expensive. Another approach to the problem of aldehyde neutralization is offered by commonly assigned and co-pending patent application U.S. Ser. No. 09/747,230 entitled "REDUCTIVE AMINATION FOR ALDEHYDE NEUTRALIZATION" which teaches the reaction of aldehydes with amino acid neutralizers followed by reduction of the resulting imines to form amino acids as final environmentally friendly products. This method is best carried out on solid supports and the solid waste is disposed after application. In another approach, commonly assigned and copending patent application U.S. Ser. No. 09/746,344, entitled, "DEVICE AND METHOD OF USE FOR ALDEHYDE REMOVAL", discloses using polymeric amines as scavengers to remove aldehydes from waste solutions. Although this method removes both glutaraldehyde and o-phthalaldehyde from the used disinfectant solution, the solid waste still must be handled separately.

Thus different approaches to the challenge of aldehyde neutralization are still needed for various situations. This invention is intended to offer another approach relating to neutralization of aldehydes as hereinafter described.

SUMMARY OF THE INVENTION

One embodiment of the invention relates to a method for making a neutralized aldehyde of lessened toxicity comprising the steps of:

a) providing an aldehyde; and b) contacting the aldehyde with an effective amount of an oxidizing agent to render the treated aldehyde as neutralized and less toxic compared with the untreated aldehyde.

Another embodiment of the invention relates to a system for neutralizing aldehydes and making the aldehydes less toxic comprising:

a) a container;

b) a source of aldehyde selected from the group consisting of o-phthalaldehyde, glutaraldehyde, formaldehyde and mixtures thereof directed to the container; and c) a source of oxidizing agent directed to the container to yield treated aldehydes of lower toxicity than the untreated aldehydes.

A major advantage of this invention is that it is a simple, fast, inexpensive, and non-hazardous method to neutralize aldehyde sterilization solutions. When hydrogen peroxide is used as the oxidant, it safely turns to water. The end product of oxidation of aldehydes are either colorless or lightly colored as opposed to some of the dark colored products formed by amino acid neutralization of aldehydes as explained above.

Additional features, embodiments, and benefits will be evident in view of the figures and detailed description presented below.

BRIEF DESCRIPTION OF THE DRAWINGS

The features, aspects, and advantages of the invention will become more thoroughly apparent from the following detailed description, appended claims, and accompanying drawings in which:

FIG. 1 shows the ratio of SBS:OPA and the concentration of OPA remaining in solution after 30 minutes from combining the ingredients.

DETAILED DESCRIPTION OF THE INVENTION

The invention relates to methods and compositions particularly useful for the environmentally friendly and non-reversible neutralization of aldehydes present in waste generated from sterilizing medical devices (e.g., scalpels, scissors, endoscopes, etc.) or laboratory equipment (e.g., glassware) that have been exposed to microorganisms such as bacteria. As used herein, the term non-reversible is intended to refer to the substantial prevention of the neutralized aldehyde (e.g., amino acid treated aldehyde) from reverting back to the starting or unneutralized aldehyde. Sterilizing includes disinfecting medical devices.

The neutralizer comprises oxidants. Suitable oxidants are selected from the group consisting of hydrogen peroxide, benzoyl peroxide, peroxyformic acid, peroxyacetic acid, trifluoroperacetic acid, peroxybenzoic acid, ammonium cerium nitrate, nitric acid, ammonium nitrate, potassium chromate, sodium dichromate, potassium dichromate, chlorine, sodium chlorate, sodium hypochlorite, potassium hypochlorite, calcium hypochlorite, sodium hypobromite, sodium hypoiodite, potassium hypoiodite, sodium iodate, periodic acid, sodium periodate, potassium periodate, manganese dioxide, potassium manganate, potassium permanganate, potassium persulfate, magnesium permanganate, ruthenium tetroxide and mixtures thereof.

When the oxidant is used in solution form, suitable solvents comprise water and alcohol. Suitable alcohols may include methanol, ethanol, isopropanol, n-propanol, and butanol. Water or alcohol may also contain acetone, acetonitrile, or tetrahydrofuran (THF).

Oxidants are an improvement over the typical chemicals such as ammonia or sodium bisulfite used to neutralize aldehydes since the oxidants quickly and effectively neutralize aldehydes to a level prescribed by federal and state environmental agencies. Effective amounts of the oxidant to the aldehydes will vary based on the aldehyde being neutralized and the oxidizer used.

In the case of glutaraldehyde as the aldehyde and hydrogen peroxide as the oxidizer, nonhazardous neutralization will occur when the molar ratio range of glutaraldehyde to hydrogen peroxide is typically at least about 1: 1, typically from about 1:1 to 1:100; preferably from 1:4 to 1:50, and most preferably from 1:8 to 1:16. In the case of glutaraldehyde and sodium hypochlorite as the oxidizer, nonhazardous neutralization will occur when the molar ratio range of glutaradehyde to sodium hypochlorite is typically about at least 1:1.5, typically from about 1:1.5 to 1:100; preferably from 1:2 to 1:50, and most preferably from 1:3 to 1:16.

In the case of o-phthalaldehyde as the aldehyde and hydrogen peroxide as the oxidizer, nonhazardous neutralization will occur when the molar ratio range of o-phthalaldehyde to hydrogen peroxide is typically at least about 1:0.7, typically from about 1:0.7 to 1:100; preferably from 1:1 to 1:10, and most preferably from 1:1.4 to 1:7. In the case of o-phthalaldehyde and sodium hypochlorite as the oxidizer, nonhazardous neutralization will occur when the molar ratio range of o-phthalaldehyde to sodium hypochlorite is typically at least about 1:06, typically from about 1:0.6 to 1:50; preferably from 1:0.8 to 1:5, and most preferably from 1:1 to 1:2. In the case of o-phthalaldehyde and potassium persulfate as the oxidizer, nonhazardous neutralization will occur when the molar ratio range of o-phthalaldehyde to potassium persulfate is typically at least about 1:8, typically from about 1:8 to 1:100; preferably from 1:9 to 1:50; and most preferably from 1:10 to 1:25.

To neutralize aldehydes, the oxidizer in solution or in solid form may be added to waste water that is in a tank (e.g., a neutralization tank at a waste water treatment plant), or in a small container (e.g., a bucket) where aldehydes must be neutralized before they are placed into a sewer system that may discharge to a POTW or into navigable waters. Solids contaminated with aldehydes (e.g., dirt, rags, or gloves, etc.) may be neutralized by directly adding the neutralizer to the solids or by placing the solids into a container with the neutralizer and, optionally, water.

Thus another embodiment of the invention relates to a system for neutralizing aldehydes and making the aldehydes less toxic comprising:

a) a container;

b) a source of aldehyde selected from the group consisting of o-phthalaldehyde, glutaraldehyde, formaldehyde and mixtures thereof directed to the container; and c) a source of oxidizing agent directed to the container to yield treated aldehydes of lower toxicity than the untreated aldehydes.

Additionally the system may further comprise a source of a pH adjusting material to adjust the pH of the treated aldehyde.

The source of materials suitable for use in conjunction with the systems of this invention are the same as disclosed above in the discussion relating to the methods of this invention. Additionally, the system may contain controls on any of the sources added to the container to achieve the treated aldehyde having a $LC_{50}$ greater than 500 mg/L or any other desired non-toxicity level.

EXAMPLES

Unless specified, all the reactions were performed at room temperature and concentrations are expressed on a w/v % basis except as noted and except when reference is made to 0.55% (w/w %) OPA from CIDEX® OPA Solution and 2.4% (w/w %) glutaraldehyde from CIDEX® Glutaraldehyde wherein these solution as expressed on a weight to weight basis.

Two methods were used to evaluate the extent of neutralization. The first method is the thin layer chromatography visualization ("TLC visualization") method. In general, the TLC visualization method comprises the following steps: (a) spotting a sample of the solution on the bottom of a TLC plate (usually silica plate), (b) placing the TLC plate in a solvent chamber with the plate side spotted with sample at the bottom. The solvent (usually mixed solvents) is selected so that all the components in the sample mixture is developed into isolated spots after developing (c) developing (letting the solvent climbing the TLC plate) and letting the mixture being pushed upward and separated into isolated spots (d) visualization (to show the separated spot visually with the aid of displaying agent, or fluorescence etc.). In the case of the method used in the following examples, if aldehdye was present, spots (or bands) would display a blue color with pink background upon dipping in Schiff's reagent (Fluka 84655, diluted to 10% concentration with ethanol).

The second method used was based on the visual examination of color of the solution ("Color visualization"). Glycine solution (1%) was used to detect the presence of OPA. The appearance of any green color or dark green or black green is a good indication of the presence of OPA. If only one aldehyde group was present (if the other reacted with an oxidant), other color would display upon adding glycine, such as yellow, yellowish orange or orange or even reddish colors. Although the darkness of the green-flavored color of the Schiff's base formed between glycine and OPA is good indication of OPA level, one have to keep in mind that the Schiff's base could be oxidized by many oxidants to cause darker color. Caution must be taken where comparison is needed in these situations. Although HPLC analysis is an ultimate tool for the analysis of di-aldehyde remaining, we found that the above estimation is quite sufficient for our purpose.

(A) Neutralization of Glutaraldehyde (Examples 1–8)

Example 1

To 0.5 mL of 2.4% glutaraldehyde, 0.5mL of 59% hydrogen peroxide was added at room temperature. Immediately after mixing, the resulting solution was tested by: (a) the TLC visualization method using 1% glycine, with the results not showing any green or green to dark color in a period of 1 hour; and (b) a drop of Schiff's reagent (Fluka) test solution was added, no positive results (no pink or purple color) was observed. Therefore, under the test conditions, the oxidant, hydrogen peroxide, is effective in neutralizing the glutaraldehyde.

Example 2

Into 6 beakers (50 mL) indicated below as 2-1 through 2-6, 1 mL 10% hydrogen peroxide was added, glutaraldehyde (2.4%) of different volumes, 24.53, 12.27, 6.13, 3.07, 1.53, 0.77 mL respectively, were added to beakers #2-1 through 2–6, respectively. The solutions were shaken briefly and let stand for 2 hours. Different amounts of water were added to the beakers to make them to same volumes (25.53 mL). The solutions were spotted onto a TLC silica plate on plastic (Aldrich) and dried in an oven at 75° C. for 3 minutes and developed in an ethanol: methylene chloride (1:4) solution. The plates were briefly dipped in Schiff's reagent (Fluka) (diluted to 10% with ethanol) and heated in an oven (75° C.) for 5 minutes to visualize (blue spots with pink background). The oxidant to aldehyde mole ratio and volume ratio are summarized in Table 2. Vial "R" was 2.4% glutaraldehyde used as reference. Results indicated that, under the test conditions, 2 volumes of 10% $H_2O_2$ is effective to neutralize 3 volumes of 2.4% glutaraldehyde.

TABLE 2

Effect of Hydrogen Peroxide (10%) and Glutaraldehyde (2.4%) Mixing Ratio

| Exp. # | 2-1 | 2-2 | 2-3 | 2-4 | 2-5 | 2-6 | R |
|---|---|---|---|---|---|---|---|
| Vol (10% $H_2O_2$):Vol (2.4% Glutaraldehyde) | 1:25 | 1:12 | 1:6 | 1:3 | 1:1.5 | 1:0.77 | Ref. |
| $H_2O_2$:Glutaraldehyde Mole Ratio | 1:2 | 1:1 | 2:1 | 4:1 | 8:1 | 16:1 | |
| TLC visualization | Spot size decreases from exp. 1 to 4 (All smaller than reference spot) Some glutaraldehyde left | | | | No spot No glutaraldehyde left | | |

Example 3

From Example 2, the solution of 2-2 (hydrogen peroxide: glutaraldehyde volume ratio 1:12 and mole ratio 1:1) was used. After mixing of 10% hydrogen peroxide (1 mL) and 2.4% glutaraldehyde (12.27 mL), 1 mL of the mixed solution was mixed with 0.2 mL 1N sodium hydroxide solution. After standing at room temperature overnight, no glutaraldehyde was left based on the TLC result (same TLC condition). Adding base helped the oxidation.

Example 4

Same as in Example 3, but 0.2 mL 10% hydrochloric acid was used instead of sodium hydroxide. Glutaraldehyde level did not significantly drop after standing at room temperature overnight as seen from TLC result. Adding acid did not significantly promote the oxidation.

Example 5

To 1.0 mL of glutaraldehyde (2.4%) (un-activated), 0.5 mL household bleach (5% NaOCl) was added and the solution gradually turned yellow. The oxidation reaction was followed by TLC visualization at 5 minutes and 20 minutes. The solutions were spotted onto a TLC silica plate on plastic (Aldrich) and was blown with air for 1 minute before developing in an ethanol: methylene chloride (5:95(V/V)) solution. The plates were briefly dipped in Schiff's reagent (Fluka) (diluted to 10% with ethanol) and heated in an oven (75° C.) for 5 minutes to visualize blue spots with a pink background indicating glutaraldehyde was still present. Most of the glutaraldehyde was not oxidized in 5 minutes while almost all the glutaraldehyde was oxidized in 20 minutes.

Example 6

To 6 vials (2 mL) indicated below as 6-1 through 6-6, 100, 200, 350, 500, 650 and 800 μL bleach (5% sodium hypochlorite) were added respectively. Glutaraldehyde (2.4%) of different volumes, 900, 800, 650, 500, 350 and 200 μL were added to beakers 6-1 through 6-6, respectively (Table 3). The solutions were shaken briefly and allowed to stand for 20 minutes. The solutions were spotted onto TLC silica plate on plastic (Aldrich) and was blown with air for 1 minute before being developed in an ethanol: methylene chloride (5:95(V/V)) solution. The plates were dipped in Schiff's reagent (Fluka) (diluted to 10% with ethanol) briefly and heated in oven (75° C.) for 5 minutes to visualize blue spots with pink background. Vial "R" was 2.4% glutaraldehyde control. The colors of solutions indicate the amount of oxidation which has taken place. The levels of the blue spots on the TLC plate indicate the relative remaining of un-oxidized or un-neutralized glutaraldehyde. The results indicated equal volumes of bleach (5% NaOCl) can effective neutralize 2.4% glutaraldehyde in 20 minutes.

TABLE 3

Effect of Bleach (5% NaOCl) and Glutaraldehyde (2.4%) Mixing Ratio

| Exp. # | 6-1 | 6-2 | 6-3 | 6-4 | 6-5 | 6-6 | R |
|---|---|---|---|---|---|---|---|
| 5% NaOCl (μL) | 100 | 200 | 350 | 500 | 650 | 800 | Ref. |
| 2.4% Glut.(μL) | 900 | 800 | 650 | 500 | 350 | 200 | Glutaldehyde |
| NaOCl:Glut. Mole Ratio | 0.31:1 | 0.70:1 | 1.51:1 | 2.8:1 | 5.2:1 | 11.2:1 | |
| TLC Visualization | Most glutaraldehyde left | Some glutaraldehyde left | Little glutaraldehyde left | | No glutaraldehyde left | | |

Example 7

The same experiment in Example 6 was repeated with the aid of additional base. The added base slightly promotes the glutaraldehyde oxidation (from the darker colors in Vials 6-2, 6-3 and 6-4 solutions and a little lighter colors of the corresponding blue TLC spots).

TABLE 4

Same as Table 3 with Additional Base (20 minutes reaction time).

| Exp. # | 6-1 | 6-2 | 6-3 | 6-4 | 6-5 | 6-6 | R |
|---|---|---|---|---|---|---|---|
| 5% NaOCl (μL) | 100 | 200 | 350 | 500 | 650 | 800 | Ref. |
| 1N NaOH (μL) | 10 | 10 | 10 | 10 | 10 | 10 | Glut |
| 2.4% Glut (μL) | 900 | 800 | 650 | 500 | 350 | 200 | |
| NaOCl:NaOH:Glut Mole Ratio | 0.31:0.046:1 | 0.70:0.052:1 | 1.51:0.064:1 | 2.802:0.083:1 | 5.20:0.12:1 | 11.2:0.21:1 | |
| TLC visualization | Most glutaraldehyde left | Some glutaraldehyde left | Little glutaraldehyde left | | No glutaraldehyde left | | |

Example 8

The same experiment in Example 7 was repeated with longer reaction time (6 hours instead of 20 minutes). It was found that no further oxidation occurred beyond the levels in that of Example 7. This is an important finding that it supports that the oxidation of glutaraldehyde is fast. Although the reaction time is important during the first 20 minutes, it appears no longer important after that. On the other hand, the amount of the oxidants, such as bleach or hydrogen peroxide, is crucial.

TABLE 5

Same as Table 4 with Extended Time (6 hours instead of 20 minutes)

| Exp. # | 6-1 | 6-2 | 6-3 | 6-4 | 6-5 | 6-6 | R |
|---|---|---|---|---|---|---|---|
| 5% NaOCl (μL) | 100 | 200 | 350 | 500 | 650 | 800 | Ref. |
| 1N NaOH (μL) | 10 | 10 | 10 | 10 | 10 | 10 | Glutaraldehyde |
| 2.4% Glut (μL) | 900 | 800 | 650 | 500 | 350 | 200 | |
| NaOCl:NaOH:Glut Mole Ratio | 0.31:0.046:1 | 0.70:0.052:1 | 1.51:0.064:1 | 2.802:0.083:1 | 5.20:0.12:1 | 11.2:0.21:1 | |
| TLC Visualization | Most glutaraldehyde left | Some glutaraldehyde left | Little glutaraldehyde left | | No glutaraldehyde left | | |

(B) Neutralization of OPA (Examples 9 –13)

Example 9

In 6 vials (2 mL) indicated below as 9-1 through 9-6, 100, 200, 350, 500, 650 and 800 μL of hydrogen peroxide (10% hydrogen peroxide) was added respectively, OPA (0.55%) of different volumes, 900, 800, 650, 500, 350 and 200 μL were added to beakers 9-1 through 9-6, respectively (Table 6). The solutions were shaken briefly and allowed to stand for 20 minutes. The solutions were spotted onto TLC silica plate on plastic (Aldrich) and was blown with air for I minute before developing in an ethanol: methylene chloride (5:95 (V/V)) solution. The plates were briefly dipped in Schiff's reagent (Fluka) (diluted to 10% with ethanol) and heated in an oven (75° C.) for 5 minutes for visualization to determine if any spotting resulted (to see black spots with pink background). Only the reference OPA showed a black spot. To further confirm this result, 200 μL 1.0% glycine was added into each vial and the color visualized in 5 minutes. Only the reference OPA gave a green-black color and all the others do not show a color. One may question if hydrogen peroxide would destroy the Schiff's base and therefore its color. To confirm this, to 0.5 mL of the Schiff's base solution (obtained from mixing the reference 1.0 mL of 0.55% OPA with 200 μL 1.0% glycine at room temperature for 5 minutes), 500 μL 10% hydrogen peroxide was added and mixed. The resulting color was even darker. Therefore, the above method is valid (Schiff's base was not destroyed by hydrogen peroxide).

TABLE 6

Oxidation of 0.55% OPA with 10% Hydrogen Peroxide

| Exp. # | 9-1 | 9-2 | 9-3 | 9-4 | 9-5 | 9-6 | R |
|---|---|---|---|---|---|---|---|
| 10% $H_2O_2$ (μL) | 100 | 200 | 350 | 500 | 650 | 800 | Ref. |
| 0.55% OPA (μL) | 900 | 800 | 650 | 500 | 350 | 200 | OPA |
| $H_2O_2$:OPA Mole Ratio | 8.0:1 | 17.9:1 | 38.6:1 | 71.7:1 | 133.2:1 | 286.8:1 | |
| TLC Visualization | No OPA left (No TLC black spot) | | | | | | |
| Color Visualization after Mixing w/1% Glycine | No OPA left (No dark-green color of Schiff's base) | | | | | | |

Example 10

Oxidation of 0.55% OPA with 10% Hydrogen Peroxide (Less Amount of Oxidant).

What is the minimum amount of hydrogen peroxide needed to neutralize per volume of 0.55% OPA? Example 9 was repeated using much less amount of hydrogen peroxide (Table 7). The same procedure was followed. After addition of glycine, only the Vial 9-6 showed dark green color, i.e., there was OPA not neutralized in this vial. OPA in all the other vials were all neutralized. The results indicated that only 2% volume of 10% hydrogen peroxide can be used to effectively neutralize 0.55% OPA. The volume of hydrogen peroxide can be reduced with more concentrated hydrogen peroxide solution.

TABLE 7

Neutralization of 0.55% OPA with 10% Hydrogen Peroxide (With less oxidant)

| Exp. # | 9-1 | 9-2 | 9-3 | 9-4 | 9-5 | 9-6 | R |
|---|---|---|---|---|---|---|---|
| 10% $H_2O_2$ (μL) | 100 | 80 | 60 | 40 | 20 | 10 | Ref. |
| 0.55% OPA (μL) | 1000 | 1000 | 1000 | 1000 | 1000 | 1000 | OPA |
| $H_2O_2$:OPA Mole Ratio | 7.171:1 | 5.737:1 | 4.302:1 | 2.868:1 | 1.434:1 | 0.717:1 | |
| Color Visualization after Mixing w/1% Glycine | No OPA left (No dark-green color of Schiff's base) | | | | | Little OPA left | |

Example 11

The similar experiment as that for Example 6 (except color visualization was used instead of TLC visualization) was conducted with 5% potassium persulfate as the oxidant (Aldrich 37,982-4, lot 21028BN) and OPA as the aldehyde (Table 8).

TABLE 8

Oxidation of 0.55% OPA with 5% Potassium Persulfate

| Exp. # | 6-1 | 6-2 | 6-3 | 6-4 | 6-5 | 6-6 | R |
|---|---|---|---|---|---|---|---|
| 5% $K_2S_2O_8$ (μL): | 100 | 200 | 350 | 500 | 650 | 800 | Ref. |
| 0.55% OPA (μL) | 900 | 800 | 650 | 500 | 350 | 200 | OPA |
| $K_2S_2O_8$:OPA Mole Ratio | 0.501:1 | 1.128:1 | 2.430:1 | 4.512:1 | 8.380:1 | 18.049:1 | |
| Color Visualization after Mixing w/1% Glycine | Some OPA left | | | | Little OPA left | No OPA left | |

Example 12

Oxidation of 0.55% OPA with Bleach (5% Sodium Hypochlorite) The similar experiment as that for Example 6 (except TLC was not used) was conducted with household bleach 5% sodium hypochlorite and OPA as the aldehyde (Table 9). It could be concluded that oxidation was complete in all the vials. Based on this data, the bleach amount could be further reduced.

TABLE 9

Oxidation of 0.55% OPA with Household Bleach (5% sodium hypochlorite)

| Exp. # | 6-1 | 6-2 | 6-3 | 6-4 | 6-5 | 6-6 | R |
|---|---|---|---|---|---|---|---|
| 5% NaOCl (μL) | 100 | 200 | 350 | 500 | 650 | 800 | Ref. |
| 1N NaOH (μL) | 10 | 10 | 10 | 10 | 10 | 10 | OPA |
| 0.55% OPA (μL) | 900 | 800 | 650 | 500 | 350 | 200 | |
| NaOCl:NaOH:OPA Mole Ratio | 1.820:0.271:1 | 4.096:0.305:1 | 8.822:0.375:1 | 16.383:0.375:1 | 30.425:0.488:1 | 65.532:0.697:1 | |
| Color Visualization after Mixing w/1% Glycine | No OPA left | | | | | | |

Example 13

Oxidation of 0.55% OPA with Bleach (5% Sodium Hypochlorite) (Less Amount of Oxidant).

Example 12 was repeated using much less amount of bleach and the results are shown in Table 10. The same procedure was followed. After addition of glycine for 5 minutes, only the Vials 6-5 and 6-6 showed a dark green color, i.e., there was OPA not neutralized in these 2 vials. Based on our understanding of OPA/Glycine Schiff's base color behaviors, we know there was only trace amount of OPA un-neutralized in the Vial 6-4. Thus, based on Vial 6-3, about 6% volume bleach (5% sodium hypochlorite) can be used to neutralize of 0.55% OPA. This is a very desired result considering the inexpensive price of household bleach and the absence of concern of disposing bleach to the drain. If 10–13% sodium hypochlorite was used, only 3% volume will be needed.

TABLE 10

| Oxidation of OPA (0.55%) with Bleach (5% Sodium Hypochlorite) (With less oxidant). | | | | | | | |
|---|---|---|---|---|---|---|---|
| Exp. # | 6-1 | 6-2 | 6-3 | 6-4 | 6-5 | 6-6 | R |
| 5% NaOCl (µL) | 100 | 80 | 60 | 40 | 20 | 10 | Ref. |
| 0.55% OPA (µL) | 1000 | 1000 | 1000 | 1000 | 1000 | 1000 | OPA |
| NaOCl:OPA Mole Ratio | 1.638:1 | 1.311:1 | 0.983:1 | 0.655:1 | 0.328:1 | 0.164:1 | |
| Color Visualization after Mixing w/1% Glycine | No OPA left | | | Little OPA left | Some OPA left | | |

(C) Fish Tests

Example 14

Fish Tests

California Code Regs ("CCR") Title 22-Fathead Minnow Hazardous Waste Screen Bioassay.

The following tests were conducted to determine whether aldehydes neutralized by the oxidant, hydrogen operoxide, was hazardous under the Californian regulation except that a more stringent concentration of 750 mg/L was used instead of the 500 mg/L concentration of the Californian regulation.

(a) Hydrogen peroxide (5%) failed fish test (0% survival at 750mg/L concentration in 48 hours).

(b) OPA (125 mL, 0.55%) and hydrogen peroxide (25 mL, 5.0%) were mixed thoroughly and waited for 20 minutes before fish test. The mole ratio of OPA to $H_2O_2$ is 1 to 7.2. Test results indicated that 2 out of the 10 fish died in 48hours (80% survival) and 4 out of the 10 fish died in 96 hours (60% survival). Thus, this composition would surpass the less stringent Californian regulations.

(c) OPA (250 mL, 0.55%) and hydrogen peroxide (83.3 mL, 3.0%) were mixed thoroughly and waited for 20 minutes before fish test. The mole ratio of OPA to $H_2O_2$ is 1 to 7.2. The results indicated that all fish survived the challenge (100% survival in 750 mg/L concentration after 96 hours) and exceeded the Californian regulations.

In the preceding detailed description, the invention is described with reference to specific embodiments thereof. It will, however, be evident that various modifications and changes may be made thereto without departing from the broader spirit and scope of the invention as set forth in the claims. The specification and drawings are, accordingly, to be regarded in an illustrative rather than a restrictive sense.

What is claimed is:

1. A system for neutralizing aldehydes and making the aldehydes less toxic comprising:

a) a container;

b) a source of aldehydes; and c) a source of oxidizing agent directed to the container to yield treated aldehydes of lower toxicity than the untreated aldehydes.

2. The system of claim 1, wherein the oxidizing agent is selected from the group consisting of hydrogen peroxide, benzoyl peroxide, peroxyformic acid, peroxyacetic acid, trifluoroperacetic acid, peroxybenzoic acid, ammonium cerium nitrate, nitric acid, ammonium nitrate, potassium chromate, sodium dichromate, potassium dichromate, chlorine, sodium chlorate, sodium hypochlorite, potassium hypochlorite, calcium hypochlorite, sodium hypobromite, sodium hypoiodite, potassium hypoiodite, sodium iodate, periodic acid, sodium periodate, potassium periodate, manganese dioxide, potassium manganate, potassium permanganate, potassium persulfate, magnesium permanganate, ruthenium tetroxide and mixtures thereof.

3. The system of claim 1, wherein the oxidizing agent is hydrogen peroxide.

4. The system of claim 3, wherein the hydrogen peroxide is in solution form.

5. The system of claim 3, wherein the hydrogen peroxide is in solid form.

6. The system of claim 1, wherein the oxidizing agent is potassium persulfate.

7. The system of claim 1, wherein the oxidizing agent is sodium hypochlorite.

8. The system of claim 1 further comprising a source of diluent.

9. The system of any one of claims 1–8, wherein the sources added to the container are controlled to achieve the treated aldehydes having a toxicity level of $LC_{50}$ greater than 500mg/L.

* * * * *